United States Patent
Takada et al.

(10) Patent No.: US 10,342,964 B2
(45) Date of Patent: Jul. 9, 2019

(54) MICRONEEDLE PREPARATION ADMINISTRATION MEMBER FOR PLACEMENT OF OBJECTIVE SUBSTANCE IN DERMIS, AND APPARATUS FOR QUICK ADMINISTRATION OF MICRONEEDLE PREPARATION

(71) Applicants: BIOSERENTACH CO., LTD., Kyoto (JP); LABO JUVERSA CO., LTD., Hokkaido (JP)

(72) Inventors: Kanji Takada, Kyoto (JP); Ichiro Ono, Hokkaido (JP)

(73) Assignee: Labo Juversa Co., Ltd., Hokkaido (JP)

( * ) Notice: Subject to any disclaimer, the term of this patent is extended or adjusted under 35 U.S.C. 154(b) by 19 days.

(21) Appl. No.: 15/124,387

(22) PCT Filed: Mar. 12, 2014

(86) PCT No.: PCT/JP2014/056473
§ 371 (c)(1),
(2) Date: Sep. 8, 2016

(87) PCT Pub. No.: WO2015/136639
PCT Pub. Date: Sep. 17, 2015

(65) Prior Publication Data
US 2017/0014608 A1      Jan. 19, 2017

(51) Int. Cl.
*A61M 37/00* (2006.01)
*A61K 9/00* (2006.01)
(Continued)

(52) U.S. Cl.
CPC ....... *A61M 37/0015* (2013.01); *A61K 9/0014* (2013.01); *A61K 38/1825* (2013.01);
(Continued)

(58) Field of Classification Search
CPC ...... A61M 37/0015; A61M 2037/0023; A61M 2037/0046; A61M 2037/0061;
(Continued)

(56) References Cited

U.S. PATENT DOCUMENTS

2007/0260201 A1* 11/2007 Prausnitz .............. A61F 9/0017
                                                           604/272
2008/0262444 A1   10/2008 Takada
(Continued)

FOREIGN PATENT DOCUMENTS

CN      101505816       8/2009
CN      101868229       10/2010
(Continued)

OTHER PUBLICATIONS

Patent translate: Translation of JP 5709223, dated Dec. 20, 2017.*
(Continued)

*Primary Examiner* — Bradley J Osinski
*Assistant Examiner* — Nilay J Shah
(74) *Attorney, Agent, or Firm* — Wenderoth, Lind & Ponack, L.L.P.

(57) ABSTRACT

The invention is a microneedle preparation administration apparatus comprising: a guide tube; a pedestal in which at least a part thereof including a front end surface is housed within the guide tube and slides in length direction; and driving means for driving the pedestal toward a front end part of the guide tube, and microneedle preparations being to be attached to the front end surface of the pedestal.

13 Claims, 6 Drawing Sheets

(51) Int. Cl.
*A61K 38/18* (2006.01)
*A61K 38/00* (2006.01)

(52) U.S. Cl.
CPC ...... *A61K 38/00* (2013.01); *A61M 2037/0023* (2013.01); *A61M 2037/0046* (2013.01); *A61M 2202/07* (2013.01); *A61M 2202/097* (2013.01)

(58) Field of Classification Search
CPC .......... A61M 2202/07; A61M 2202/30; A61M 2202/097; A61B 17/205
See application file for complete search history.

(56) References Cited

U.S. PATENT DOCUMENTS

| | | | | |
|---|---|---|---|---|
| 2009/0216215 | A1* | 8/2009 | Thalmann | A61M 5/158 604/506 |
| 2011/0028905 | A1* | 2/2011 | Takada | A61K 9/0021 604/180 |
| 2011/0276027 | A1 | 11/2011 | Trautman et al. | |
| 2013/0072902 | A1 | 3/2013 | Takada et al. | |
| 2013/0296790 | A1 | 11/2013 | Masaoka et al. | |

FOREIGN PATENT DOCUMENTS

| | | |
|---|---|---|
| CN | 103298520 | 9/2013 |
| JP | 2008-510520 | 4/2008 |
| JP | 2012-75855 | 4/2012 |
| JP | 2012-509106 | 4/2012 |
| JP | 2012-254952 | 12/2012 |
| JP | 2013-27492 | 2/2013 |
| JP | 2013-525078 | 6/2013 |
| JP | 2013-226472 | 11/2013 |
| WO | 2006/023684 | 3/2006 |
| WO | 2006/080508 | 8/2006 |
| WO | 2008/022476 | 2/2008 |
| WO | 2009/066763 | 5/2009 |
| WO | 2009/107806 | 9/2009 |
| WO | WO 2009107806 A2 * | 9/2009 ........ A61M 37/0015 |
| WO | 2010/059605 | 5/2010 |
| WO | 2011/140240 | 11/2011 |
| WO | 2012/057345 | 5/2012 |
| WO | 2012/088154 | 6/2012 |
| WO | 2013/002331 | 1/2013 |

OTHER PUBLICATIONS

International Search Report dated Jun. 24, 2014 in International Application No. PCT/JP2014/056473.
Notification of Transmittal of Translation of the International Preliminary Report on Patentability (Chapter I or Chapter II) dated Sep. 22, 2016 in International (PCT) Application No. PCT/JP2014/056473.
English translation of Written Opinion of the International Searching Authority dated Jun. 24, 2014 in International (PCT) Application No. PCT/JP2014/056473.
Extended European Search Report dated Oct. 9, 2017 in corresponding European patent application No. 14885596.8.

* cited by examiner

MICRONEEDLE PREPARATION ADMINISTRATION MEMBER FOR PLACEMENT OF OBJECTIVE SUBSTANCE IN DERMIS, AND APPARATUS FOR QUICK ADMINISTRATION OF MICRONEEDLE PREPARATION

TECHNICAL FIELD

The present invention relates to a self-dissolving microneedle transdermal absorption preparation, which retains a drug, which self-dissolves when it is inserted into or placed in skin thereby allowing the skin to absorb the drug, and at the same time relates to an apparatus for quick administration of a self-dissolving microneedle transdermal absorption preparation.

BACKGROUND ART

There are microneedles for the pharmaceutical technology for improving absorption rates of drugs that are extremely low in permeability to the stratum corneum layer of skin. Microneedles are needles that are miniaturized to such an extent that one does not feel pain even if the skin is punctured with them. The microneedles generally have a length of 1 mm or less.

These microneedles have similar hollow structures to injection needles. They are of a type in which a drug solution is injected, or are made of a biodegradable polymer such as polylactic acid. Furthermore, dissolving microneedles using a water-soluble polymer substance as a base have also been developed. That is, an objective substance is retained in the water-soluble substance as the base. After inserted into skin, the base is dissolved by water in the skin, so that the objective substance may be transdermally administered.

For example, Patent Document 1 discloses that a self-dissolving microneedle is formed using, as a base, a polymer substance which is bio-soluble and thread-forming. Patent Document 2 discloses that a microneedle is divided into a part to be inserted into a living body and a pressing part, and that an objective substance is retained only in the part to be inserted into the living body in order to improve bioavailability of the objective substance contained in the microneedle.

Also, Patent Documents 1 and 2 disclose a sheet-shaped microneedle preparation administration member, in which the plurality of microneedles are formed on a platform such as a patch sheet. Use of the microneedle preparation administration member makes it possible to apply a microneedle preparation to a wide area of skin with less labor.

In the present specification, unless otherwise stated, the microneedle preparation means a self-dissolving transdermal absorption preparation which retains a drug, and self-dissolves when inserted into skin, thereby allowing the skin to absorb the drug. Unless otherwise stated, the microneedle preparation administration member means a microneedle preparation administration member, in which the plurality of microneedle preparations are formed on a platform. Specific examples of the microneedle preparation administration member include a microneedle (preparation) sheet, a microneedle (preparation) patch, a microneedle (preparation) chip, a microneedle (preparation) array sheet, a microneedle (preparation) array patch, a microneedle (preparation) array chip and the like.

Patent Document 3 discloses that by using a microneedle preparation for prevention or treatment of skin aging, or treatment of skin scars, long-term stability of an effective component is achieved, and that this allows a physician or a patient himself or herself to administer the effective component to the site of action in the skin easily, efficiently and equally, so that one may benefit from advantages such as alleviation of skin scars and rejuvenation of skin in early stage after the treatment.

However, when the microneedle preparation is used for prevention or treatment of skin aging, or treatment of skin scars, the necessity for optimization of delivery depth of the objective substance has been revealed. For example, in case of providing treatment with the use of a microneedle preparation containing bFGF, melanocytes distributed in a basal layer in epidermis of skin, that are on an administration route when the microneedle preparation is administered directly into dermis in a transdermal manner, are stimulated, and pigmentation as a side effect is caused. In order to prevent the reaction, it is preferred to realize a state in which the objective substance is absent in the vicinity of a basal layer in epidermis and a papillary layer in dermis while an only objective substance-containing portion is inserted and placed in a reticular layer in dermis or in a sub-papillary layer in dermis which are at the targeted depth in the dermis.

The microneedle has highest insertion ability when pressed while standing it upright, right angle to skin surface. Therefore, a development of an administration apparatus, which presses a microneedle preparation from direction perpendicular to skin has been made.

For example, Patent Document 4 discloses an instrument for administration of a microneedle preparation, the instrument comprising: a tubular cylinder; and a piston for supporting a microneedle preparation administration member within the cylinder, wherein the piston is pressed by a finger to move the microneedle preparation in outlet direction of the cylinder, so that it is brought into press contact with a skin surface. Furthermore, Patent Document 5 discloses an instrument for administration of a microneedle preparation, the instrument comprising: a guide tube; a support rod for supporting the microneedle preparation within the guide tube; and means for driving the support rod toward skin.

There are irregularities on a surface of a body, and irregularities on the face are very noticeable. When a large size microneedle preparation administration member is applied to a surface with irregularities, microneedles which are not pressed perpendicularly thereto increase, resulting in the occurrence of many insertion failures. When the microneedle preparation is applied to an area with irregularities, the area to be applied is divided into administration sites, each of which may be regarded as flat, and then it is required to press the microneedle preparation administration member from an optimal direction for each divided administration site.

Considering an embodiment for actually providing treatment, the size of the microneedle preparation administration member would not be enlarged to the area which may be regarded as flat on the surface of the body. When the area to be applied is larger than that, an operation of sequentially administering a plurality of microneedle preparation administration members is required.

When a plurality of microneedle preparation administration members are sequentially administered, duplicate administration to skin causes overdosing of bFGF, resulting in that a predetermined effect is not obtained, or that the probability of side effects such as inducing pigmentation becomes higher. In this case, particularly in the case of a circular or elliptical microneedle preparation administration member, avoiding duplication inevitably generates a part where administration would not be made contrary to that, so that an optimal therapeutic effect would not be expected.

Since a large number of melanocytes are distributed in an epidermal layer of skin, if a growth factor such as bFGF is administered to the epidermal layer or nearby it, the pigment producing melanocytes are stimulated to produce melanin thus causing pigmentation as the side effect. The bFGF affects a lot of fibroblasts distributed in a dermal layer of skin and let them proliferate to exhibit a regeneration effect of the skin. Therefore, a seemingly paradoxical objective that bFGF surely be delivered to the dermal layer, need to be realized. Furthermore, an area of skin on which regeneration treatment is to be conducted is specified, and it is desired that the treatment is evenly conducted through the area. Therefore, bFGF microneedle preparation administration members need to be administered sequentially without causing duplicate administration within a specified area.

In general, it takes several hours for the self-dissolving microneedle transdermal absorption preparation to dissolve completely after it is inserted into the skin. Therefore, it is required that the microneedle preparation administration member be pressed for several tens of minutes after administration. However, the administration process that requires long time causes delay in treatment, there is a problem in practical use.

PRIOR ART DOCUMENTS

Patent Documents

Patent Document 1: WO 2006/0805008 A1
Patent Document 2: WO 2009/066763 A1
Patent Document 3: WO 2013/002331 A1
Patent Document 4: WO 2009/107806 A2
Patent Document 5: JP 2012-075855 A

SUMMARY OF THE INVENTION

Problem to be Solved by the Invention

The present invention solves the above problem, and an object thereof is to provide a microneedle preparation administration apparatus, which prevents overdose administration to an area of skin to be treated caused by duplicate administration, which administers a prescribed dose of growth factor as an objective substance at an intended optional depth in the dermis equally and more reliably, and which realizes quick treatment while avoiding the side effect of pigmentation.

Means for Solving the Problem

In order to achieve the above seemingly paradoxical objective, a bilayered microneedle preparation in which only a tip end part (a first portion) of the microneedle contains an objective substance, and a bottom part (a second portion) thereof contains no objective substance is used. The bilayered microneedle preparation is prepared so that a joint part (a boundary part) between the first layer and the second layer, or a position a little closer to the bottom part becomes brittle.

The microneedle preparation administration apparatus is designed so that the bilayered microneedle is instantaneously broken by an impact pressure added at the time of administration and then the first portion is able to be placed in the dermis. At the same time, the microneedle preparation administration apparatus is designed so that the first portion of a microneedle is able to be surely inserted into an optional deep part of the dermis, which is a targeted part to be treated, by changing the impact pressure added at the time of administration.

The present invention provides a microneedle preparation administration apparatus comprising:
a guide tube having an open front end part and an at least partially closed rear end part;
a pedestal having a front end surface perpendicular and flat to length direction of the guide tube in which at least a part thereof including the front end surface is housed within the guide tube and slides in the length direction; and
driving means for driving the pedestal toward the front end part of the guide tube, and
microneedle preparations being to be attached to the front end surface of the pedestal, and the microneedle preparations being to be pressed out from the front end part of the guide tube, wherein
the microneedle preparation has a first portion having a tip end part and containing an objective substance, and a second portion having a bottom part and not containing the objective substance, and
the front end surface of the pedestal is struck on skin at a collision pressure of 30 N to 200 N per 1 $cm^2$.

In one embodiment, the first portion of the microneedle preparation contains a strength regulator.

In one embodiment, the guide tube has a cross-sectional surface perpendicular to the length direction of polygonal shape.

In one embodiment, the polygonal shape is quadrangle.

In one embodiment, the front end surface of the pedestal has the same shape as a cross-sectional surface perpendicular to the length direction of the guide tube.

In one embodiment, the guide tube has a flange perpendicular to the length direction at the front end part.

In one embodiment, the microneedle preparation is attached to the front end surface of the pedestal in the form of a microneedle preparation administration member having a platform and a plurality of microneedle preparations each retaining the objective substance.

In one embodiment, the driving means is a helical spring installed between a rear end surface of the pedestal and the rear end part of the guide tube.

In one embodiment, the guide tube further has a stopper for fixing the pedestal to the guide tube so that a position of the front end surface of the pedestal is held rearward of the front end part of the guide tube.

In one embodiment, the objective substance is at least one selected from the group consisting of various growth factors having action on skin cells, and substances promoting production of such a growth factor in skin cells.

In one embodiment, the objective substance includes a basic fibroblast growth factor (bFGF), an acidic fibroblast growth factors (aFGF), nucleic acids and plasmids encoding genes thereof, or substances stimulating and promoting their generation.

In one embodiment, the first portion has an inserting-direction length of 300 μm or less, preferably 200 μm or less, and more preferably 150 μm or less from the tip end part of the microneedle preparation.

In one embodiment, the microneedle preparation has an inserting-direction length of 100 to 1000 μm.

In one embodiment, the objective substance is delivered into a dermal layer as a target for any treatment.

In any of the microneedle preparation administration apparatuses, by imparting an impact pressure using as a driving source a spring pressure, an electrically generated pressure, and a gas pressure, the microneedle preparation, in which the object substance is contained in only the tip end part, may be instantaneously broken in the form in which an object substance-containing portion (the first portion) and a slight part of a microneedle portion (the second portion) in proximity thereof not containing the objective substance are included so that the objective substance is able to be inserted into and placed in the dermis.

In any of the microneedle preparation administration apparatuses, changing the impact pressure in the range of 30 N to 70 N per 1 $cm^2$ enables the microneedle preparation to be broken at a position a little closer to the bottom part from the boundary part between the first portion containing the objective substance and the second portion, and enables the objective substance to be placed for treatment at a shallow part in the dermis when the impact pressure is low and at a deeper part in the dermis when the impact pressure is high.

Any of the microneedle preparation administration apparatuses enables the microneedle preparation containing the objective substance, which is to be administered into the dermis, to be surely administered into the dermis.

Any of the microneedle preparation administration apparatuses includes various shapes including a pistol type having a similar function to a piston type in addition to what is shown in FIG. 1. Depending on the position and shape of the part to be treated, those devices in which a shooting part is rotated, or a microneedle gripping part is made replaceable so as to facilitate disinfection or made disposable are also included.

The present invention provides a microneedle preparation administration member having a platform and a plurality of microneedle preparations, each retaining an objective substance, wherein the microneedle preparation has a first portion having a tip end part and containing an objective substance, and a second portion having a bottom part and not containing the objective substance, the microneedle preparation administration member is used by being attached to the front end surface of the pedestal of the transdermal absorption preparation administration apparatus according to any one of the above, and a major surface of the platform has the same shape as the front end surface of the pedestal.

In one embodiment, the first portion of the microneedle preparation contains a strength regulator.

In the specification of the present application, the "length direction" means length direction of the guide tube. In the specification of the present application, the "cross-sectional surface" means a cross-sectional surface perpendicular to length direction of the guide tube. Furthermore, in the specification of the present application, the "front end" means an end in the direction from which the microneedle preparation is pressed out, and the "rear end" means an end of the bottom part opposite thereto.

Effects of the Invention

According to the present invention, a microneedle preparation administration apparatus which prevents overdose administration to an area of skin to be treated caused by duplicate administration, and which equally and more reliably administers a prescribed dose of growth factor at an intended optional depth in the dermis so as to avoid the side effect of pigmentation is provided.

In the microneedle preparation administration apparatus of the present invention, by imparting a predetermined collision pressure when the microneedle preparation is administered, it is broken simultaneously with insertion into skin, so that the tip end part containing the objective substance may be placed within the skin. As a result, it becomes possible to provide uniform treatment excellent in reproducibility quickly, efficiently and sequentially.

DESCRIPTION OF EMBODIMENTS

Figure 1:
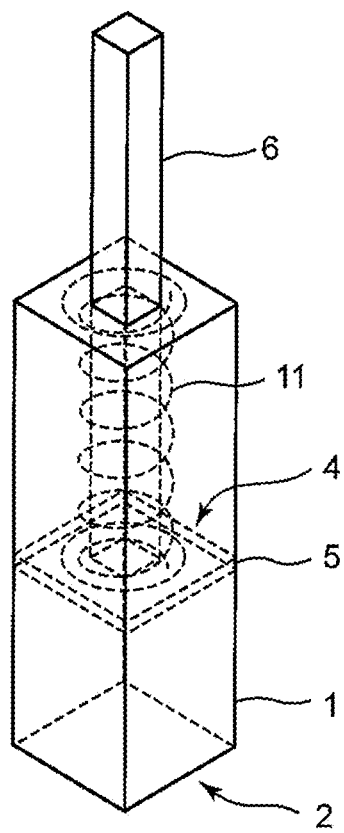
FIG. 1 is a perspective view showing the structure of a microneedle preparation administration apparatus as an embodiment of the present invention.

FIG. 1 is a perspective view showing the structure of a microneedle preparation administration apparatus as an embodiment of the present invention. The microneedle preparation administration apparatus consists of three parts. A first portion is a guide tube 1. The guide tube 1 has an open front end part 2, and a microneedle preparation is pressed out from the front end part at the time of administration. A rear end part of the guide tube is at least partially closed. The guide tube has a quadrangular prism shape. The guide tube 1 has a cross-sectional surface of quadrangular shape. Among the quadrangles, those which may be arranged on a plane without any gaps are preferred. From this point of view, the preferred quadrangle is a square.

The cross-sectional shape of the guide tube is not limited to the quadrangles, and may be polygons that may be arranged on a plane without any gaps. Specific examples of such polygons include a triangle, a pentagon, a hexagon and the like. A circular shape, an elliptic shape are also selected depending on their usages. In that case, the shape of a front end surface of a pedestal and the shape of a major surface of a platform of a microneedle preparation administration member, which are described below, become a polygonal shape, a circular shape, or an elliptic shape corresponding to the cross-sectional shape of the guide tube. Furthermore, the shape of the guide tube becomes a polygonal column, a cylinder, or an elliptic column corresponding to the cross-sectional shape.

Figure 2:
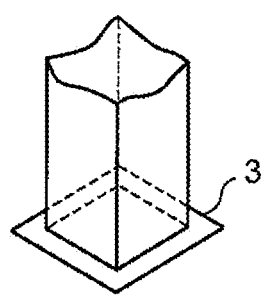
FIG. 2 is a partial perspective view showing an example of a front end part of a guide tube having a flange.

Referring to FIG. 2, the guide tube 1 preferably has, at the front end part, a flange 3 which is perpendicular to length direction. The flange 3 is brought into contact with skin whose surface is an object to be administered at the time of administration of the microneedle preparations. This makes it easier for the guide tube to be placed with the length direction thereof being perpendicular to the body surface. An adhesive may be provided on a surface of the flange 3 in order to achieve a reliable contact with the skin.

Parts that are in contact with a patient's skin, such as the front end of the guide tube and the flange, may be designed to be removable for replacement. This may save labor for disinfection, or may eliminate waste due to disposal of the entire guide tube.

A second portion is a pedestal 4 to a front end surface of which microneedle preparations are attached. The pedestal 4 has the front end surface perpendicular and flat to the length direction. The front end surface has a quadrangular shape. The front end surface preferably has the same shape as the cross-sectional surface of the guide tube. Dimensions of the front end surface are such that it may be housed inside the guide tube, and that the pedestal is substantially prevented from rotating around an axis in the length direction inside the guide tube. The substantial rotation herein means such an extent that a microneedle stabbing position, in particular a boundary of an area to be administered is not fixed, resulting in a decline in treatment accuracy.

As to dimensions of the pedestal, the longest side of the quadrangle, that is the front end surface, is 6 cm or less, preferably 0.5 mm to 3 cm, and more preferably 1 cm to 2.5 cm. If the dimensions of front end surface of the pedestal are too small, the number of administration times increases, resulting in an increase of labor. If they are too large, it is not possible to suit with unevenness or irregularity of the body surface, so that insertion failure of microneedles frequently occurs.

The shape and dimensions of the pedestal 4 are not limited as long as it is perpendicular in the length direction, has a front end surface to which microneedle preparations may be attached, and may slide in the length direction within the guide tube while keeping the front end surface perpendicular to the length direction. For example, it may be a configuration in which a plate 5 having a front end surface is supported by a thinner rod-like column or plunger rod 6.

Figure 3:
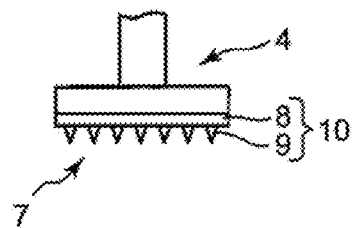
FIG. 3 is a side view of a pedestal to which microneedle preparations are attached when viewed from lateral direction.

FIG. 3 is a side view of the pedestal to which microneedle preparations are attached when viewed from lateral direction. Microneedle preparations 7 are attached to the front end surface of the pedestal 4 preferably in the form of a microneedle preparation administration member 10 having a platform 8 and a plurality of microneedles 9 each retaining the objective substance. The microneedle preparations are formed on a front surface of the platform, and a back surface of the platform is attached to the frond end surface of the pedestal 4. Preferably, the major surface (namely, the front surface or the back surface) of the platform 8 has the same shape as the front end surface of the pedestal. The microneedle preparation administration member 10 almost has the same cross sectional dimensions as or smaller cross sectional dimensions than the pedestal so as to be housed in the guide tube without any trouble.

Figure 4:
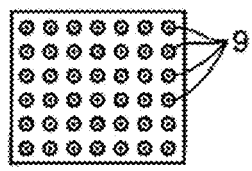
FIG. 4 is a plan view of the pedestal to which the microneedle preparations are attached when viewed from tip end direction.

FIG. 4 is a plan view of the pedestal to which microneedle preparations are attached when viewed from tip end direction. The microneedles preparations 9 are lined up equally to a longitudinal edge and a lateral edge of the front end surface of the pedestal. Therefore, when a plurality of microneedle preparation administration members are sequentially administered, positioning and administration are enabled so as not to overlap a previously administered part and so as not to generate a gap. In order to achieve the objective more efficiently, the present apparatus includes an apparatus which enables the direction of a plunger part to be freely changed by selecting a flexible material for the plunger rod, and connecting it to a drive unit according to the position and shape of a part to be treated.

Attachment of the microneedle preparations to the front end surface of the pedestal is conducted through the platform of the microneedle preparation administration member. For example, using adhesive members such as an adhesive, a pressure-sensitive adhesive and a double-coated tape, the front end surface of the pedestal and the back surface of the platform are bonded. In this case, it is necessary to adjust adhesion force appropriately so that the microneedle preparations may be separated from the pedestal after they have been struck on the skin.

In one preferred embodiment, the back surface of the platform is bonded to the front end surface of the pedestal using a magnetic force. This enables the attachment and removal of the microneedle preparations to be performed very easily and quickly. For example, a magnet is attached to the front end surface of the pedestal, and a magnetically responsive material such as iron is attached to or contained therein.

The platform of the microneedle preparation administration member may be a flexible sheet or a hard chip. It is preferred that the sheet as the platform is made of a material having high strength. For example, a paper-made plate, various medical tapes such as a wound dressing made of cloth may be adopted. The chip as the platform is preferably a porous substrate. If the platform is porous, in the process of forming microneedle preparations, the microneedle preparations are not prevented from drying. The more preferred is a tablet substrate produced in a similar manner to tablets using a tableting excipient. The reason therefor is that it is superior in productivity, and is suitable for the production process of pharmaceuticals such as sterilization. The tableting excipient may be a composition containing a plurality of components. Examples of the preferred tableting excipient include cellulose acetate, crystalline cellulose, cellulose derivatives, chitin and chitin derivatives, and the like.

A molded product composed of the tableting excipient may be produced in a similar manner to tablets. For example, the tableting excipient is placed in a mortar, and tableted at an appropriate tableting pressure using a pestle. Dimensions of the platform are adjusted as necessary by increasing or decreasing the diameter of the mortar, the filling amount of the tableting excipient and the tableting pressure. With regard to the tablet substrate, the disclosure contents of US 2011/0152792 A1 and JP 2011-12050 A are inserted here.

When magnetic responsiveness is imparted to the chip, iron powder may be mixed with the tableting excipient. For example, a magnetically responsive component is mixed with the tableting excipient, the mixture is put in a mortar, and tableted at an appropriate tableting pressure using a pestle. Dimensions of the chip are adjusted by increasing or decreasing the diameter of the mortar, the filling amount of the tableting excipient and the tableting pressure as necessary. When the chip is produced using a water-insoluble polymer such as cellulose acetate, it is preferred to form a bilayered tablet structure so that a magnetically responsive component such as iron powder is not mixed with a first layer that forms a microneedle. With regard to the tablet substrate using magnetic responsiveness, the disclosure contents of JP 2013-169432 A are inserted here.

As for the shape of the platform, for example, the major surface (namely the front surface or back surface) is a quadrangle (for example, a square) with one side of 6 cm or less, preferably 0.5 mm to 3 cm, more preferably 1 cm to 2.5 cm. The thickness of the platform is 0.1 to 10 mm, preferably 0.2 to 5 mm, and more preferably 0.3 to 3 mm. The hardness of the platform prepared from the tableting excipient is not particularly limited as long as it does not substantially deform when the microneedle preparations are stabbed into skin, and as long as it is not disintegrated when the microneedle preparations are stabbed into skin by applying a predetermined impact force.

A third part is driving means 11 for driving the pedestal toward the front end part of the guide tube. The reason therefor is that pressing force of the microneedles is easily adjusted to be constant, thus facilitating control of insertion depth compared with a case where the pedestal is manually driven. Preferably, using as a driving force for driving the pedestal, a repulsive force of a compressed spring, an expansion force such as compressed air or compressed nitrogen gas, an explosive force using gunpowder and the like, the impact pressure set may be imparted repeatedly and reliably. It is more preferred to use an elastic member such as a spring or a rubber as the driving force.

In the microneedle preparation administration apparatus, when a plurality of microneedle preparation administration members are sequentially administered, it is possible to determine a next administration site so as not to overlap a previously administered part and so as not to generate a gap. Furthermore, in the microneedle preparation administration member, the pedestal would not rotate around the axis in the length direction inside the guide tube, so that a shift of a microneedle stabbing position, in particular of the boundary of the area to be administered is reduced. These results make it possible to adjust the dose of the microneedle preparations per unit area accurately and enhance the treatment accuracy, which consequently enable quick and uniform treatment.

The microneedle preparation administration apparatus of the present invention may be provided with a stopper mechanism for fixing the pedestal to the guide tube so that a position of the front end surface of the pedestal is held rearward of the front end part of the guide tube. On this occasion, it is preferred to set a plurality of fixation positions for the pedestal. By doing so, the pressing force of the microneedle preparations to skin may be adjusted stepwise. For example, a combined use with microneedles with a multilayer structure makes it possible to accurately adjust the administration site of the objective substance according to the depth direction of skin.

Figure 5:
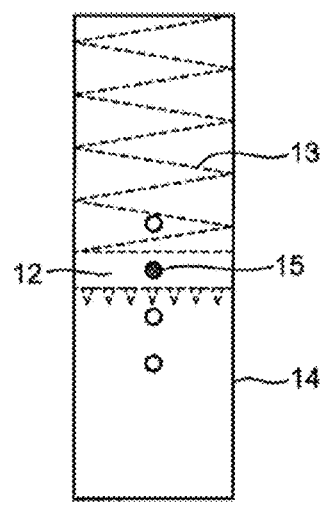
FIG. 5 is a side view showing an example of a stopper mechanism for fixing the pedestal to the guide tube.

FIG. 5 is a side view showing an example of the stopper mechanism for fixing the pedestal to the guide tube. Referring to FIG. 5, a plurality of openings are formed in a side surface of a guide tube 14, and an opening is formed also in a side wall of a plate 12. The plate 12 is pressed into the guide tube 14 while contracting a helical spring 13, the opening of the plate 12 is aligned with an opening in the side surface of the guide tube 14, and, from outside of the guide tube, a rod 15 is inserted thereinto, so that the plate 12 is fixed within the guide tube.

Figure 6:
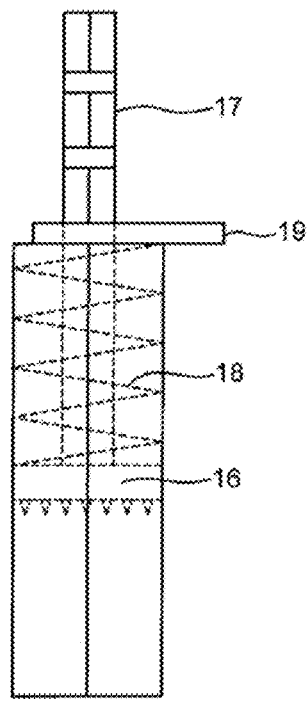
FIG. 6 is a side view showing another example of the stopper mechanism for fixing the pedestal to the guide tube.

FIG. 6 is a side view showing another example of the stopper mechanism for fixing the pedestal to the guide tube. Referring to FIG. 6, a plurality of notches for position fixation are formed at one of the four corners of a plunger rod 17. The plunger rod 17 is taken out from an upper end opening of the guide tube, pulled up while contracting a helical spring 18, a notch is aligned with a rear end of the tube, and a plate 19 as a stopper is inserted into the notch of the plunger, so that the plate 16 is fixed within the guide tube.

For the configuration of the present apparatus, besides the piston type shown in FIG. 1, various configurations having a similar function to this including a hand gun type are included.

When the microneedle preparation is used for prevention or treatment of skin aging, or treatment of skin scars, delivery of the objective substance only into dermis provides a predetermined effect, and pigmentation does not occur. On the other hand, if it is delivered into epidermis to the vicinity of a basal layer, pigmentation occurs. In order to deliver the objective substance located in a tip end part (for example, a first portion) of the dissolving microneedle preparation, there is required that a microneedle preparation administration apparatus is able to control the punctuation depth, and is able to break the microneedles at a boundary part so that only the first portion is surely placed at a targeted depth in the dermis. The punctuation depth into skin may be controlled by adjusting the collision pressure on the skin. Therefore, the relationship between the collision pressure on a patient's skin and the pigmentation was studied.

As a result, the following has been known. If the collision pressure of the microneedle preparation administration member on the skin is adjusted to 30 N per 1 $cm^2$ or higher, when about 500 μm-long microneedles are used, a tip end of each microneedle preparation is stabbed into skin to a depth of 450 μm or more, and only a first portion thereof is instantaneously broken due to the impact so as to be able to be placed at the target depth in the dermis. At this time, it has been shown that the higher the impact pressure is set, the deeper the first portion of the microneedle preparation is inserted into the dermis so as to be able to be placed. From the above results, by using the microneedle preparation administration member and the apparatus for quick administration of the microneedle preparation of the present invention, efficient and uniform administration may be realized quickly. Specifically, although 20 minutes or more was required to administer one sheet of the microneedle preparation administration member, it has become possible to complete it within one second or less. Its significance is very high in the clinical environment where quick and continuous treatment is desired.

In the structure of human skin, an epidermal layer, which is covered on a dermal layer, has a thickness of about 50 to 100 μm. Therefore, the objective substance may be delivered to the predetermined depth in the skin reliably, quickly and evenly by adjusting the collision pressure of the microneedle preparation administration member on the skin, the inserting-direction length of the microneedle preparation, and the inserting-direction length of the first portion containing the objective substance as necessary. As a result, the delivery to only the dermal layer as the target site is enabled while avoiding melanocytes distributed in the basal layer in epidermis of skin.

The collision pressure of the microneedle preparation administration member on the skin is 5 to 200 N per 1 $cm^2$, preferably 10 to 100 N per 1 $cm^2$, and more preferably 30 to 70 N per 1 $cm^2$. When the collision pressure is more than 200 N per 1 cm$^2$, a patient complains of a severe pain and in addition to that tissue is crushed due to strong impact. Therefore, the therapeutic objective would not be achieved.

Figure 7:
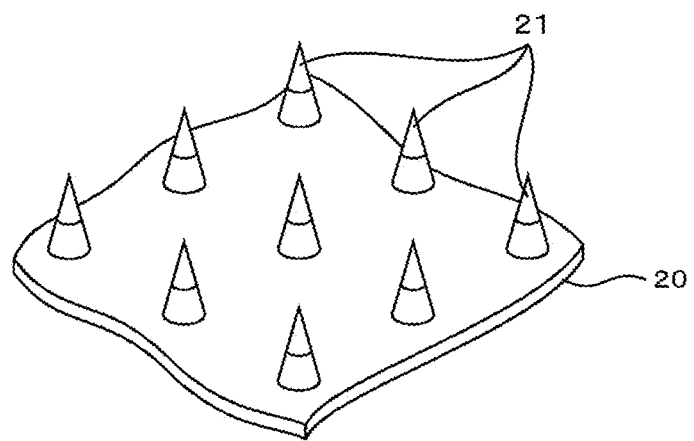
FIG. 7 is a partial perspective view showing the structure of a microneedle preparation administration member as an embodiment of the present invention.

FIG. 7 is a partial perspective view showing the structure of a microneedle preparation administration member as an embodiment of the present invention. This microneedle preparation administration member has a platform 20 and a plurality of conical microneedle preparations 21 that are formed on the platform.

For the microneedle preparation, those prepared by using preferably a water-soluble polymer substance, and more preferably a water-soluble and thread-forming polymer substance as a platform are used. In this case, it is preferred that the microneedle preparation is divided in the length direction into a plurality of areas to form a multiple-layer structure, and that the objective substance is retained only in a certain layer. The reason therefore is that the administration site may be adjusted in vertical direction, namely in the skin depth direction. As such a microneedle, one whose area is divided into two layers of a tip end part and a bottom part, and in which only the tip end part contains the objective substance is provided as an example.

Figure 8:
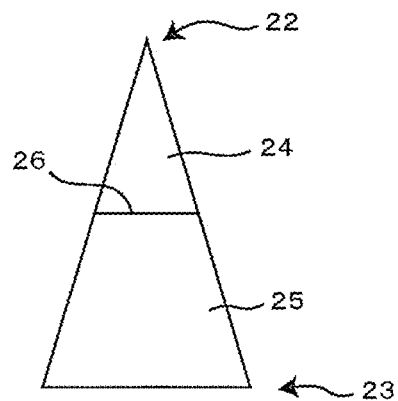
FIG. 8 is an elevational view showing an example of the microneedle preparation administration member for placement of an objective substance in the dermis.

FIG. 8 is an elevational view showing an example of a microneedle preparation used in the present invention. The microneedle is pointed and has a tip end part 22 so that it may penetrate the skin. Furthermore, the microneedle has a bottom part 23 which is large in width and is fixed to the platform. The microneedle may have a generally conical or generally pyramidal shape.

The microneedle preparation has a bottom part diameter from 30 to 1000 μm, preferably from 150 to 500 μm, and more preferably 200 to 350 μm. Also, the microneedle preparation has an inserting-direction length from 100 to 1000 μm, preferably from 250 to 750 μm, and more preferably from 400 to 600 μm. If the dimensions of the microneedle preparation are outside the range mentioned above, the microneedle may have an insufficient strength and reduced insertability. More specifically, the microneedle preparation may be conical having an inserting-direction length of 500 μm and a bottom part diameter of 300 μm.

In addition, the microneedle preparations exist on the platform in a density from 30 to 300 needles/cm$^2$, preferably from 40 to 280 needles/cm$^2$, and more preferably from 50 to 250 needles/cm$^2$. If the density of the microneedle preparation is less than 30 needles/cm$^2$, the dosage amount of the objective substance is apt to be insufficient. However, when the density of the microneedle preparations exceeds 300 needles/cm$^2$, resistance force increases during insertion of the microneedle preparations, resulting in a shallower insertion depth.

The microneedle preparation has a first portion 24 and a second portion 25. The first portion has a tip end part 22 and the second portion has a bottom part 23. The first portion and the second portion form a boundary surface 26. The boundary surface between the first portion and the second portion is generally parallel or substantially parallel with a bottom surface of the microneedle preparation.

The first portion of the microneedle preparation contains an objective substance to be administered. The second portion of the microneedle preparation does not contain the objective substance. In the present invention, the objective substance to be administered is an effective substance for prevention or treatment of skin aging or treatment of skin scars. In order to separate the first portion from the second portion at the time of administration, it is preferred to reduce the strength of the first portion, or to make the first portion more brittle so that it is easily broken by impact force. That object is achieved by containing a strength regulator.

Examples of the strength regulator that may be used include a low-molecular substance, preferably a substance hardly compatible with a base, a substance not compatible with a base, an inorganic substance, a brittle substance and the like. By containing the low-molecular substance, homogeneity of the base is hampered to reduce the strength. Examples of the low-molecular substance include an excipient for pharmaceuticals, sucrose, pH regulators (for example, monosodium phosphate, disodium phosphate, sodium dihydrogen phosphate, potassium dihydrogen phosphate, sodium hydrogen phosphate, sodium acetate, glycine, malic acid) and the like. The low-molecular substance is a substance used along with an active component, and a powdered one is used.

A saccharide may be used as the brittle substance. Specific examples of the saccharide include monosaccharides such as glucose, fructose and galactose, disaccharides such as lactose, maltose, sucrose and trehalose, polysaccharides such as dextran, starch and pullulan. Among them, dextran, in particular low molecular dextran, polyethylene glycol 2000 and the like are particularly preferred.

The first portion has an inserting-direction length equal to or shorter than a length of the microneedle inserted into the dermal layer at the time of administration of the microneedle preparation. If the first portion has an inserting-direction length exceeding the length of the microneedle preparation inserted into the dermal layer, the objective substance existing in the exceeding part is delivered to the epidermal layer. Consequently, melanocytes existing in the basal layer of epidermal layer are stimulated to cause pigmentation of the skin.

Typically, the first portion has an inserting-direction length of 300 μm or less. For example, the first portion may have an inserting-direction length of 200 μm or less, or 150 μm or less. It is not necessary to consider the lower limit of the length of the first portion. For example, in the case of an extremely small amount of a drug to be administered, the first portion may even have a length of 10 μm or less.

The microneedle preparation is typically formed of two separate portions: the first portion containing the objective substance and the second portion not containing the objective substance as shown in FIG. 2. However, the objective substance-containing portion may be altered as necessary in consideration of the site of action of the objective substance to be used. For example, when the site of action of the objective substance exists in the epidermis, the objective substance is preferably contained in the second portion.

The microneedle may have an additional separate layer between the first portion and the second portion. A plurality of layers may exist between the first portion and the second portion. When a layer is formed between the first portion and the second portion, the layer may contain the objective substance or may contain a substance exhibiting a different action from the objective substance. Concentrations of these substances may be adjusted as necessary depending on purposes.

The microneedle preparation administration member for skin treatment of the present invention is produced, for example by forming a microneedle preparation using a mold and then fixing the obtained microneedle preparation to a platform. As the mold, a plate-like stuff with holes designed to correspond to the shape and alignment of the microneedle preparations is used. Materials of the plate-like stuff used for the mold include a fluorine resin, a silicon resin, an ABS resin and the like.

First, raw materials for the first portion of the microneedle preparation, a base, an objective substance and a solvent, are mixed to prepare a first raw material mixture. The mixing amount of the strength regulator is determined as necessary in consideration of the collision pressure applied at the time of administration. On this occasion, the base is dissolved in the solvent, and the objective substance is dissolved or substantially uniformly dispersed in the solvent. Water is provided as a specific example of a preferred solvent. A polymer substance which is water-soluble and has a thread-forming property is used as the base. By using the water-soluble polymer, the microneedle preparation becomes bio-soluble to improve releasing efficiency of the objective substance in the body. The use of the thread-forming polymer enhances strength of the microneedle preparation to improve insertability into the skin.

The bio-soluble and thread-forming polymer substance to be used is at least one substance selected from the group consisting of a polysaccharide having a thread-forming property, protein, polyvinyl alcohol, carboxyvinyl polymer and sodium polyacrylate. One of these polymer substances may be used alone or several thereof may be used in combination.

Preferably, the thread-forming polysaccharide is at least one substance selected from chondroitin sulfate and salts thereof (sodium chondroitin sulfate and the like), dextran, dextran sulfate, hyaluronic acid and salts thereof (sodium hyaluronate and the like), cyclodextrin, hydroxypropyl cellulose, alginic acid, agarose, pullulan, glycogen and derivatives thereof.

Preferably, the thread-forming protein is at least one substance selected from serum albumin, serum a acidic glycoprotein, collagen, low molecular collagen, gelatin and derivatives thereof.

Particularly preferred bio-soluble and thread-forming polymer substances include sodium chondroitin sulfate, dextran, sodium hyaluronate and the like. Since these substances have been practically used as pharmaceutical products and ensured in terms of safety.

The objective substance is not particularly limited as long as it is a substance effective for prevention or treatment of skin aging or treatment of skin scars and dissolved or dispersed and retained in the above mentioned polymer substance. The objective substance may be any of various growth factors having action on skin cells, plasmids or substances promoting production of such a growth factor in skin cells.

Specific examples of such a growth factor include all proteins falling within an FGF subfamily, such as basic fibroblast growth factors (bFGF, FGF2) and acidic fibroblast growth factors (aFGF, FGF1), nucleic acids and plasmids encoding genes thereof, substances promoting their secretion and the like. Compounds expected to be used in combination with FGF: decapentaplegic (DPP), transforming growth factor (TGF) β, sonic hedge hog (shh), Wingless int (Wnt), bone morphogenetic protein (BMP), epidermal growth factor (EGF), insulin like growth factor (ILGF), platelet derived growth factor (PDGF), vascular endothelial growth factor (VEGF), hepatocyte growth factor (HGF) and the like are also included.

bFGF (FGF2) which is one of the objective substances is a well-known substance and is commercially available (e.g., bFGF product "trafermin (recombinant): Kaken Pharmaceutical Co., Ltd." and the like). bFGF may be in any form of natural or recombinant bFGF or a precursor protein thereof, a natural or recombinant bFGF protein with substitution/deletion/insertion of one or two or more of their constituent amino acids; a protein encoded by cDNA which may hybridize to cDNA of natural human bFGF under stringent conditions (65° C., 1×SSC, 0.1% SDS, or 0.1×SSC, 0.1% SDS); or a protein which has a homology of 75% or more, preferably 80% or more, more preferably 85% or more, yet preferably 90% or more, yet more preferably 95% or more to cDNA of natural human bFGF; or may be a nucleic acid encoding the gene of each protein (cDNA or cDNA plasmid; in the present invention, hereinafter collectively referred to as "gene") as long as it is effective in preventing/treating skin aging or treating skin scars in the present invention. The gene may also be used in the form of a single plasmid or in the form of a composite plasmid as an expression vector.

Expression vectors used to enhance gene transduction efficiency in the present invention include any expression vectors such as virus vectors, preferably expression vectors for mammalian cells. A promoter comprised in an expression vector used in the present invention is operably linked to bFGF gene and is functional in mammalian (preferably human) cells. The promoter may be inducible or constitutive and, if necessary, tissue-specific. It is known that the timing of expression varies depending on the kind of promoter used, and for example, each of early immediate promoter, early promoter and late promoter initiates expression of the gene under its control at its unique time. Therefore, if bFGF is administered to a mammal in the form of a gene, the timing and duration of expression of the bFGF protein may also be adjusted by properly selecting the kind of promoter.

In addition to bFGF, all FGF subfamily proteins such as aFGF (FGF1), all nucleic acids and plasmids encoding genes thereof, substances promoting production of such a growth factor in skin cells are also known to have a similar effect to bFGF. The objective substance may contain, in addition to bFGF and aFGF, other substances having or expected to have similar therapeutic effects for skin aging and skin scars together. The substances having or expected to have the above mentioned effects include morphogens such as DPP (decapentaplegic), transforming growth factor β (TGF β), Hh (Hedgehog), shh (Sonic Hedgehog), Wnt (Wingless int), bone morphogenic protein (BMP), Epidermal growth factor (EGF) and insulin-like growth factor (ILGF); platelet derived Growth Factor (PDGF), Vascular Endothelial Growth Factor (VGEF), and Hepatocyte Growth Factor (HGF).

Substances enhancing production of the growth factors in skin cells include, for example, eicosanoids such as prostaglandin, extract substances of cyclic adenosine monophosphate (cyclic AMP) and all equivalent synthetic compounds.

In addition, biocompatible substances such as polymer substances, low molecular substances, chemical substances, physiological active substances, proteins (recombinant or natural), peptides and polysaccharides may be employed as the objective substance. Peptides, proteins, nucleic acids or polysaccharides are preferable. The objective substance may be a cell, drug, vaccine, nutrient or cosmetic ingredient.

Then, the first raw material mixture is loaded onto a mold, to which, applying pressure is applied using an application tool such as a squeegee or an application apparatus, if necessary, to fill holes formed on the mold with the mixture. The mold may be centrifugalized using a centrifugal machine and the like in order to ensure the filling.

After removing the excess first raw material mixture, the mixture filled in the holes is dried. The drying step is carried out at a temperature of 50° C. or lower, preferably room temperature or lower to prevent deterioration of the objective substance, and the like. After drying, the volume of the first raw material mixture decreases.

The inserting-direction length of the first portion of the microneedle preparation may be adjusted by utilizing this phenomenon. That is, when the first raw material mixture is prepared, solid content concentration in the first raw material mixture is adjusted to an adequate concentration so that solid content of the first raw material mixture remains at a level corresponding to an objective inserting-direction length of the first portion of the microneedle after drying the first raw material mixture in the mold.

The second portion of the microneedle preparation has an inserting-direction length of preferably 100 µm or more, more preferably 200 µm or more, yet preferably 220 µm or more. On the other hand, from the viewpoint of securing enough administration amount of the objective substance, the inserting-direction length of the second portion of the microneedle preparation is preferably 400 µm or less, more preferably 300 µm or less, yet preferably 250 µm or less. In the process of formation of the first portion of the microneedle, the inserting-direction length of the first portion of the microneedle may be adjusted so that the inserting-direction length of the second portion is optimal, and also, the collision pressure may be adjusted during the treatment.

When the objective substance is bFGF, the content of the microneedle preparation is 0.1 to 5 µg, preferably 0.3 to 2.0 µg, and more preferably 0.4 to 1.5 µg per 1 cm$^2$. When the content of bFGF is less than 0.1 µg, the therapeutic effect is poor. When it is more than 5 µg, pigmentation may occur in the skin.

Then, the raw materials of the second portion of the microneedle preparation, a base and solvent, are mixed to prepare a second raw material mixture. At this time, the base is dissolved in the solvent. Water is provided as a preferred example of the solvent. Then, the second raw material mixture is loaded onto the mold filled with the dried first raw material mixture, and filled in the holes formed in the mold by using an application tool or an application apparatus if necessary. Before the second mixture is dried, a platform is placed on the mold so as to contact the second mixture. The platform is a porous plate or film, so that, when the platform contacts the second mixture, ingredients of the second mixture penetrate into pores inside the platform by anchor effect to thereby result in strong bonding therebetween, and at the same time the platform may absorb and release water contained in the second mixture. The mold may be subjected to centrifugal force by using a centrifugal machine and the like to ensure the filling. Then, the second raw material mixture filled in the holes is dried. The drying step is carried out at a temperature of 50° C. or lower, preferably room temperature or lower to prevent deterioration of the objective substance, and the like. Subsequently, the platform is removed from the mold to obtain a microneedle assembly preparation for skin treatment of the present invention.

The obtained microneedle preparation administration member for skin treatment is used to prevent or treat human or animal skin aging or treat skin scars. Administration sites typically include those which are exposed outside the body surface of a human, such as face, arms and the dorsum of hands. Symptoms to be prevented or treated in the present invention include, specifically, skin aging such as skin wrinkles, flecks, sagging, rough skin, thinning, reduced skin viscoelasticity; UV-damaged skin, (hypertrophic, atrophic) scars, keloids, acne scars, hair loss, suture wounds, burn wounds, ulcers, decubitus, diabetic ulcers, diseases requiring angiogenesis and the like.

Specific embodiments will hereinafter be described by giving examples. It is a matter of course that the present invention is not limited to the following examples.

Example 1

Referring to FIG. 1, a rectangular parallelepiped guide tube 1 having outer dimensions (length: 2.0 cm×width: 2.0 cm×height: 7.0 cm) with its lower end entirely open, and upper end having a 5 mm (length)×5 mm (height) square opening formed therein at its center was fabricated using a 3-D printer. The opening at the lower end of the guide tube 1 was a 1.7 cm (length)×1.7 cm (width) square. A longitudinally long strip-shaped opening was formed (not shown) in one side surface of the guide tube so as to be able to visually check a position of a microneedle preparation.

A pedestal 4 having a plate 5 and a plunger rod 6 was fabricated using the 3-D printer. A neodymium magnet (about 11 mm (length)×about 9 mm (width)×about 2 mm (thickness)) (not shown) was glued to a front side of the plate 5. To the plunger rod 6, a helical spring made of a stainless steel wire having a wire diameter of 0.9 mm, an outer diameter of 1.5 cm, a free height of 6.5 cm, and an effective winding number of 10 Na was attached. Thereafter, the pedestal 4 was inserted into the guide tube 1.

A mortar in a single punch tableting machine with square internal dimensions of 1.5 cm (length)×1.5 cm (width) was prepared. About 0.30 g of a 100:10:5 mixture of cellulose acetate, hydroxypropyl cellulose and iron powder was loaded onto the mortar. Subsequently, about 0.25 g of a 100:10 mixture of cellulose acetate and hydroxypropyl cellulose was loaded thereonto, and a tableting pressure of about 10 kN was applied to form a 1.5 cm (length)×1.5 cm (width)×2.0 mm (thickness) square bilayered tablet serving as a chip for substrate.

Distilled water (1 mL) was added to 880 mg of a lyophilized bFGF preparation ("FIBLAST Spray 500" (trade name), manufactured by Kaken Pharmaceutical Co., Ltd.)), 76 mg of sodium chondroitin sulfate as a base (manufactured by Maruha Nichiro Corporation), 10 mg of sucrose and 148 mg of a low molecular weight dextran ("Dextran 70" (trade name) manufactured by Meito Sangyo Co., Ltd.) as strength regulators to prepare a viscous solution. The viscous solution was applied on a female mold having 300 inverted cone pores with a depth of about 500 µm and an opening diameter of about 300 µm, per 1.6-cm square. The female mold was filled under pressurized condition, followed by drying. The female mold was filled to a height of about 200 µm from a tip end part. Thereafter, a viscous solution prepared by adding 1 mL of purified water to 1 g of sodium chondroitin sulfate was applied on the female mold again, and filled the female mold under pressurized condition.

After drying, a viscous solution prepared by adding 1 mL of purified water to 1 g of sodium chondroitin sulfate was applied on the chip for substrate, and put on the female mold and dried under pressure. After six hours, the chip for substrate was removed from the female mold to obtain a microneedle array chip with 300 microneedles formed and arranged in an array, and with magnetic responsiveness. The bFGF content per microneedle array chip was measured by HPLC and was about 0.6 µg.

Example 2

The bFGF microneedle array chip fabricated in Example 1 was attached to a square administration apparatus. The compressed spring used at that time was variously replaced, and a stopping position of a plunger was changed so that collision pressures of 30 N, 40 N, and 50 N per 1 cm$^2$ were obtained. For measurement of the collision pressures, a digital force gauge ("FGP-50" (trade name), NIDEC-SHIMPO CORPORATION) was used.

A written consent was obtained from a patient. The bFGF microneedle array chip was struck on a skin surface of the patient's face. About one second later, the chip was peeled from the skin. The collision surface of the chip was observed. With regard to substantially all the microneedles sufficiently inserted, a configuration in which they were broken at almost the same point was confirmed.

Figure 9A:
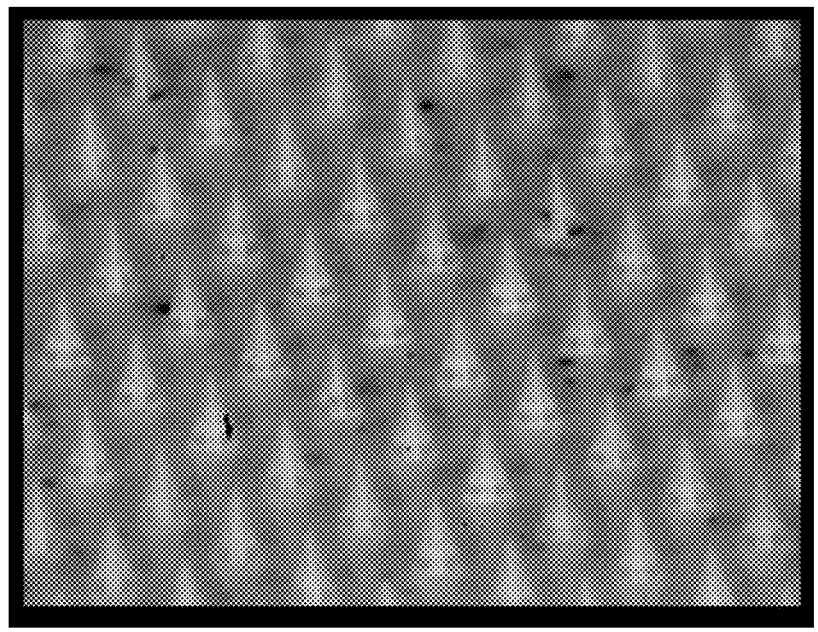
FIG. 9A is an enlarged photograph magnified about 200 times, which shows a configuration of microneedle preparations before administration.
Figure 9B:
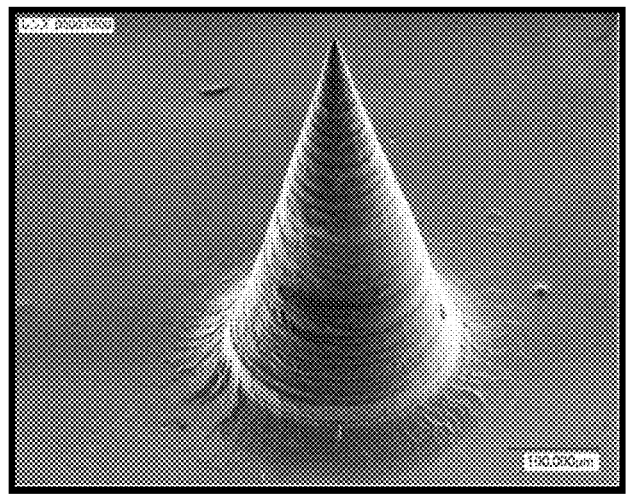
FIG. 9B an enlarged photograph magnified about 500 times, which shows a configuration of a microneedle preparation before administration.
Figure 10A:
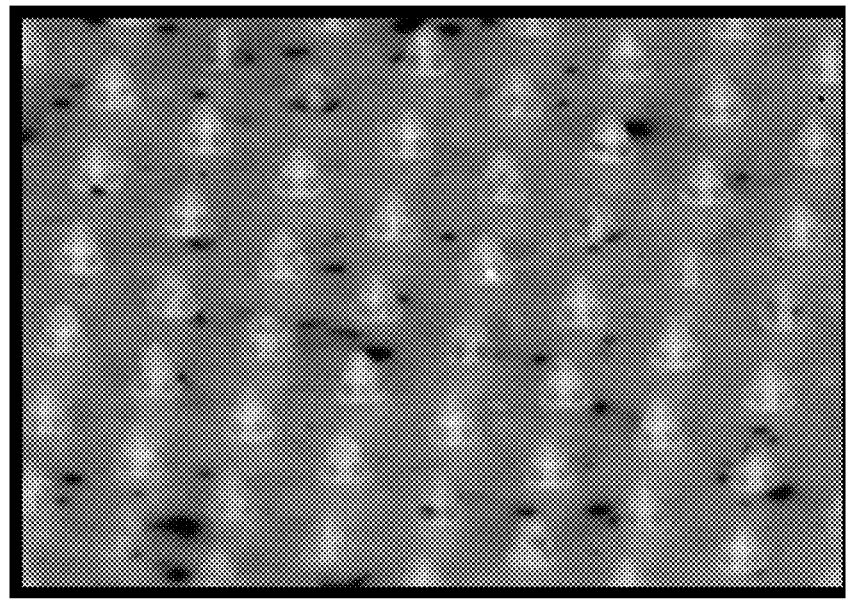
FIG. 10A is an enlarged photograph magnified about 200 times, which shows a configuration of microneedle preparations after administration.
Figure 10B:
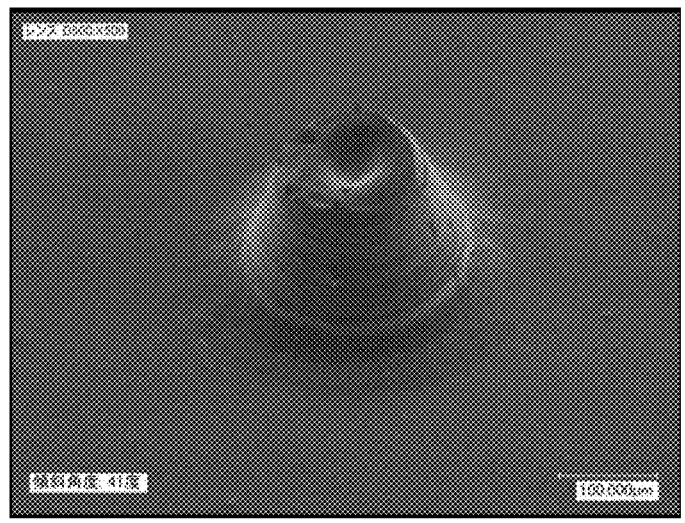
FIG. 10B an enlarged photograph magnified about 500 times, which shows a configuration of a microneedle preparation after administration.

FIG. 9A and FIG. 9B are enlarged photographs showing a configuration of microneedle preparations before administration. Each microneedle preparation before administration has an inserting-direction length of about 500 µm. FIG. 10A and FIG. 10B are enlarged photographs showing a configuration of broken microneedles after administration. Each broken microneedle has a height of 258 µm. Breakage of the microneedle occurs in the vicinity of a boundary part between the tip end part containing bFGF as the objective substance (the first portion) and the bottom part not containing bFGF (the second portion), or a position slightly closer to the bottom part from the boundary part.

Administration of the microneedle array was conducted by changing the collision pressure on the skin surface. As a result, when the collision pressure was 30 N/cm$^2$, pigmentation was caused in 15 examples out of 20. At the collision pressure of 40 N/cm$^2$, pigmentation was caused in 12 examples out of 40. On the other hand, when the collision pressure was increased to 50 N/cm$^2$, pigmentation was caused in only one example out of 20.

From the above results, it has turned out that if the skin is punctured with the bFGF microneedle array chip at an impact pressure of 50 N, the side effect of pigmentation may be prevented.

As described above, the microneedle array containing the objective substance in the tip end part is evenly inserted into the skin with good reproducibility by striking it at an appropriate collision pressure. Also, by adding the collision pressure, the microneedle array is broken at almost the same point. As a result, without the necessity to bring the microneedle array chip into pressure contact with the skin for a long time, the microneedles are instantaneously inserted into the skin to be broken, and then the objective substance-containing portion is enabled to be placed at an optional depth in the dermis.

Example 3

The bFGF microneedle array chip containing 0.6 µg of bFGF per chip, which was fabricated in Example 1, was attached to the square administration apparatus. A helical spring generating a compression pressure of 50 N/cm$^2$ was used. In a non-anesthetic state, the skin was punctured with five microneedle array chips one after another along with patient's nasolabial folds, who sat on an examination table, over one minute. The patient's skin was observed after 1, 3, and 6 months. There was no pigmentation, and a considerable improvement in the texture of the skin was observed.

DESCRIPTION OF REFERENCE NUMERALS

1 . . . guide tube
2 . . . front end part
3 . . . flange
4 . . . pedestal
5 . . . plate
6 . . . plunger rod
7, 21 . . . microneedle preparation
8, 20 . . . platform
9 . . . microneedle
10 . . . microneedle preparation administration member
11 . . . driving means
22 . . . tip end part
23 . . . bottom part
24 . . . first portion
25 . . . second portion
26 . . . boundary surface

The invention claimed is:

1. A microneedle preparation administration apparatus comprising:
   a guide tube having an open front end part and an at least partially closed rear end part;
   a pedestal having a front end surface perpendicular and flat to a length direction of the guide tube, in which at least a part thereof including the front end surface is housed within the guide tube and slides in the length direction;
   a driving means for driving the pedestal toward the front end part of the guide tube; and
   microneedle preparations being configured to be attached to the front end surface of the pedestal, and being configured to be pressed out from the front end part of the guide tube, wherein
   each of the microneedle preparations is self-dissolving,
   each of the microneedle preparations has a first portion having a tip end part and containing an objective substance, and a second portion having a bottom part and not containing the objective substance, wherein a strength of the first portion is reduced compared with a strength of the second portion and/or the first portion is made to be more brittle than the second portion,
   the first portion and the second portion form a boundary surface,
   the boundary surface between the first portion and the second portion is substantially parallel with a bottom surface of the microneedle preparations,
   the second portion is formed on top of a platform and the first portion is formed on top of the second portion such that only a part of the second portion is in contact with the first portion and the first portion does not directly contact the platform, and
   the front end surface of the pedestal is configured to strike a skin at a collision pressure that inserts the microneedle preparations into the skin and breaks the first portion and a part of the second portion including the boundary surface due to the collision.

2. The microneedle preparation administration apparatus according to claim 1, wherein the first portion of the microneedle preparations contains a strength regulator agent.

3. The microneedle preparation administration apparatus according to claim 2, wherein the strength regulator agent is a substance selected from the group consisting of glucose, fructose, galactose, lactose, maltose, sucrose, dextran, starch pullulan and polyethylene glycol.

4. The microneedle preparation administration apparatus according to claim 1, wherein the collision pressure is 5 N to 200 N per cm$^2$.

5. The microneedle preparation administration apparatus according to claim 1, wherein the microneedle preparations are attached to the front end surface of the pedestal in the form of a microneedle preparation administration member having the platform and the microneedle preparations each retaining the objective substance.

6. The microneedle preparation administration apparatus according to claim 1, wherein the driving means is a helical spring, an electrically driven means or a gas pressure installed between a rear end surface of the pedestal and the rear end part of the guide tube.

7. The microneedle preparation apparatus according to claim 1, wherein the guide tube further has a stopper for fixing the pedestal to the guide tube so that a position of the front end surface of the pedestal is held rearward of the front end part of the guide tube.

8. The microneedle preparation administration apparatus according to claim 1, wherein the objective substance is at least one selected from the group consisting of various growth factors having action on skin cells, and substances promoting production of such a growth factor in skin cells.

9. The microneedle preparation administration apparatus according to claim 1, wherein the objective substance includes a basic fibroblast growth factor (bFGF), an acidic fibroblast growth factors (aFGF), nucleic acids and plasmids encoding genes thereof, or substances stimulating and promoting their generation.

10. The microneedle preparation administration apparatus according to claim 1, wherein the first portion has an inserting-direction length of 300 μm or less from the tip end part of each of the microneedle preparations.

11. The microneedle preparation administration apparatus according to claim 1, wherein the microneedle preparations have an inserting-direction length of 100 μm to 1000 μm.

12. A microneedle preparation administration member having a platform and a plurality of the microneedle preparations, each retaining the objective substance, wherein each of the microneedle preparations is self-dissolving, each of the microneedle preparations has the first portion having the tip end part and containing the objective substance, and the second portion having the bottom part and not containing the objective substance, wherein the strength of the first portion is reduced compared with the strength of the second portion and/or the first portion is made to be more brittle than the second portion, the first portion and the second portion form a boundary surface, the boundary surface between the first portion and the second portion is substantially parallel with a bottom surface of the microneedle preparations, the second portion is formed on top of the platform and the first portion is formed on top of the second portion such that only a part of the second portion is in contact with the first portion and the first portion does not directly contact the platform, and the microneedle preparation administration member is configured to be attached to the front end surface of the pedestal of the microneedle preparation administration apparatus according to claim 1, and a major surface of the platform has a same shape as the front end surface of the pedestal.

13. The microneedle preparation administration member according to claim 12, wherein the first portion of the microneedle preparation contains a strength regulator agent.

* * * * *